(12) United States Patent
Nino et al.

(10) Patent No.: US 9,241,751 B2
(45) Date of Patent: Jan. 26, 2016

(54) CANNULATED TORQUE DEVICE AND TIP ENGAGEMENT

(75) Inventors: John Nino, Simi Valley, CA (US); David Ivinson, Camarillo, CA (US)

(73) Assignee: ECA Medical Instruments, Thousand Oaks, CA (US)

( * ) Notice: Subject to any disclaimer, the term of this patent is extended or adjusted under 35 U.S.C. 154(b) by 91 days.

(21) Appl. No.: 13/812,328

(22) PCT Filed: Jul. 21, 2011

(86) PCT No.: PCT/US2011/044840
§ 371 (c)(1),
(2), (4) Date: Feb. 6, 2013

(87) PCT Pub. No.: WO2012/015660
PCT Pub. Date: Feb. 2, 2012

(65) Prior Publication Data
US 2013/0226192 A1    Aug. 29, 2013

Related U.S. Application Data

(60) Provisional application No. 61/368,519, filed on Jul. 28, 2010.

(51) Int. Cl.
| | | |
|---|---|---|
| A61B 17/58 | (2006.01) | |
| A61B 17/60 | (2006.01) | |
| A61F 2/00 | (2006.01) | |
| A61B 17/88 | (2006.01) | |
| A61B 19/00 | (2006.01) | |
| B25B 13/46 | (2006.01) | |
| B25B 23/14 | (2006.01) | |
| B25B 23/142 | (2006.01) | |

(52) U.S. Cl.
CPC ............. *A61B 17/8875* (2013.01); *A61B 19/30* (2013.01); *B25B 13/466* (2013.01); *B25B 23/141* (2013.01); *B25B 23/1427* (2013.01); *A61B 2019/301* (2013.01)

(58) Field of Classification Search
CPC ...................... A61B 17/8875; A61B 2019/301
See application file for complete search history.

(56) References Cited

U.S. PATENT DOCUMENTS

| | | | | |
|---|---|---|---|---|
| 5,423,819 A * | 6/1995 | Small et al. | .................... | 606/232 |
| 7,197,968 B2 * | 4/2007 | Bubel | ................ | A61B 17/8875 |
| | | | | 192/56.62 |
| 7,334,509 B1 * | 2/2008 | Gao | ........................ | B25B 15/02 |
| | | | | 81/467 |
| 7,475,619 B2 * | 1/2009 | Chiu | ..................... | B25B 13/483 |
| | | | | 81/467 |
| 7,503,443 B1 * | 3/2009 | Dobras | ................. | B25B 23/141 |
| | | | | 192/48.6 |
| 7,762,164 B2 * | 7/2010 | Nino et al. | ....................... | 81/475 |
| 7,938,046 B2 * | 5/2011 | Nino et al. | ....................... | 81/475 |
| 8,365,641 B2 * | 2/2013 | Daglow | ............. | B25B 23/1427 |
| | | | | 81/467 |
| 8,408,104 B2 * | 4/2013 | Lin | ......................... | B25B 15/00 |
| | | | | 81/467 |
| 2006/0179981 A1 | 8/2006 | Cutler et al. | | |
| 2006/0278051 A1 | 12/2006 | Gauthier et al. | | |
| 2008/0161814 A1 * | 7/2008 | McAllister | ............. | A61B 17/86 |
| | | | | 606/83 |
| 2009/0248035 A1 | 10/2009 | Sjostedt | | |

(Continued)

FOREIGN PATENT DOCUMENTS

JP       2007-68970 A       3/2007

*Primary Examiner* — Olivia C Chang
(74) *Attorney, Agent, or Firm* — Baker Hostetler LLP; Mark H. Krietzman

(57) ABSTRACT

A cannulated torque-limiting device with one or more lumen therein which may mate with an additional operational tool. An A-O tip engagement for receiving and securing tips and tools for varying applications and needs is also disclosed.

3 Claims, 14 Drawing Sheets

(56) References Cited

U.S. PATENT DOCUMENTS

2009/0293687 A1* 12/2009 Nino .................. B25B 23/1427
  81/476
2012/0055296 A1* 3/2012 Landowski ......... B25B 23/1427
  81/474
2013/0152746 A1* 6/2013 Kerboul ............. A61B 17/8875
  81/475
2013/0327190 A1* 12/2013 Laurenti ............. B25B 23/1427
  81/475

* cited by examiner

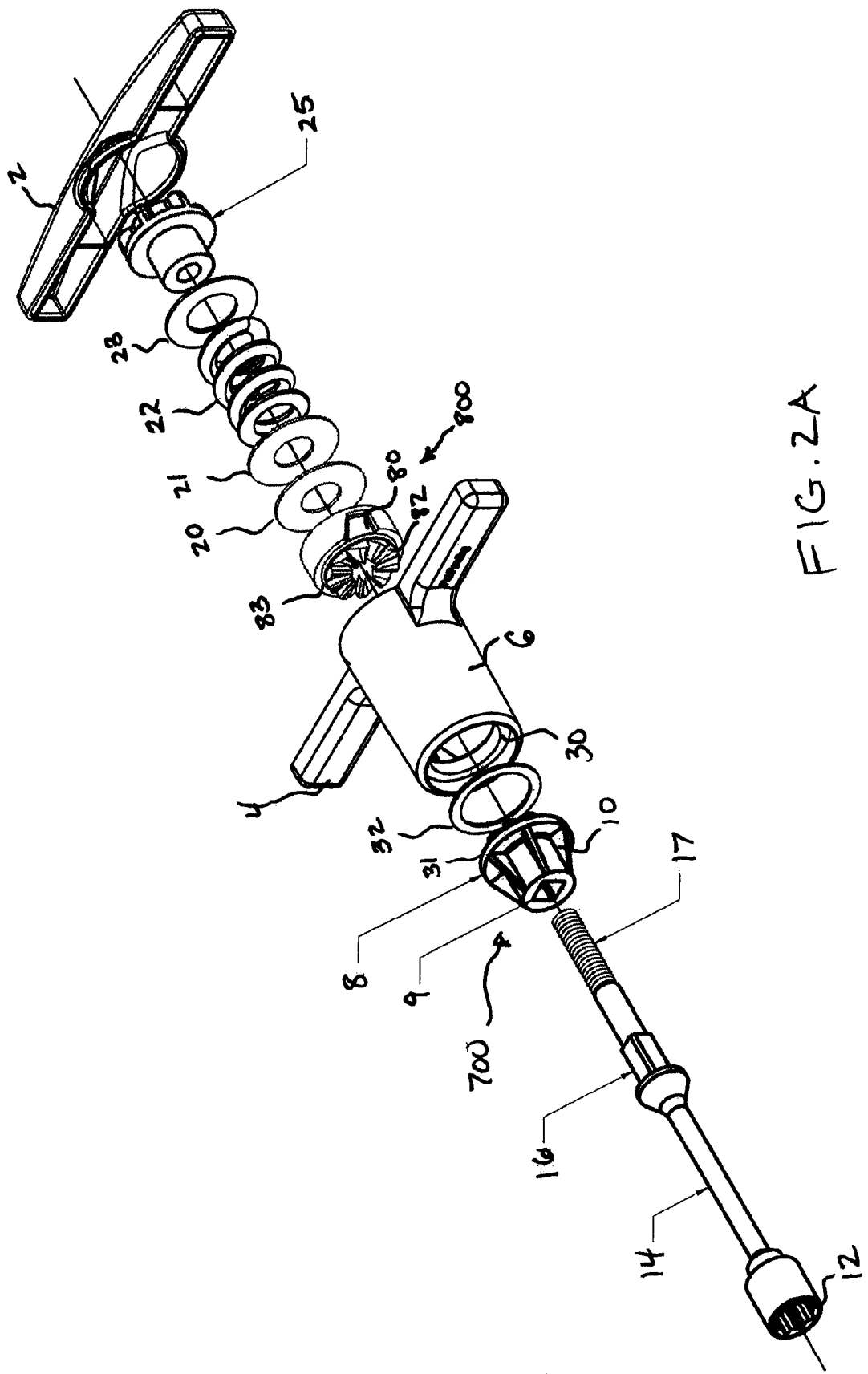

CANNULATED TORQUE DEVICE AND TIP ENGAGEMENT

CROSS-REFERENCE TO RELATED APPLICATIONS

This application is a National Stage of International patent application PCT/US2011/044840, filed on Jul. 21, 2011, which claims priority to U.S. provisional patent application No. 61/368,519, filed on Jul. 28, 2010, the disclosures of which are incorporated by reference in their entirety.

RELATED APPLICATION

This application claims the full Paris Convention benefit of and priority U.S. Provisional Patent Application Ser. No. 61/368,519, filed Jul. 28, 2010, the contents of which are incorporated by reference herein in their entirety, as if fully set forth herein.

BACKGROUND

1. Field

This disclosure relates to a driver tool and, in particular, to a medical use torque-limiting driver that disengages at a predetermined torque limit.

2. General Background

Torque is a measure of force acting on an object that causes that object to rotate. In the case of a driver and a fastener, this measurement can be calculated mathematically in terms of the cross product of specific vectors:

$$\tau = r \times F$$

Where r is the vector representing the distance and direction from an axis of a fastener to a point where the force is applied and F is the force vector acting on the driver.

Torque has dimensions of force times distance and the SI unit of torque is the Newton meter (N-m). The joule, which is the SI unit for energy or work, is also defined as an N-m, but this unit is not used for torque. Since energy can be thought of as the result of force times distance, energy is always a scalar whereas torque is force cross-distance and so is a vector-valued quantity. Other non-SI units of torque include pound-force-feet, foot-pounds-force, ounce-force-inches, meter-kilograms-force, inch-ounces or inch-pounds.

Torque-limiting drivers are widely used throughout the medical industry. These torque-limiting drivers have a factory pre-set torque to ensure the accuracy and toughness required to meet a demanding surgical environment.

The medical industry has made use of both reusable and disposable torque-limiting drivers. In a surgical context, there is little room for error and these drivers must impart a precise amount of torque.

Reusable drivers require constant recalibration to ensure that the driver is imparting the precise amount of torque. Recalibration is a cumbersome task but must be done routinely. Such reusable devices also require sterilization.

Disposable drivers are an alternative to the reusable drivers. Once the driver has been used, it is discarded.

Disposable drivers are traditionally used for low torque applications. The standard torque values in these applications typically range from about 4 to about 20 inch-ounces. It has, however, been a challenge to develop a reliable disposable driver capable of imparting higher torques for larger applications.

Piecemeal drivetrain systems have been developed to gear-up or otherwise impart greater torque with disposable devices. Such piecemeal systems provide interchangeability of parts to a device, within which torque is transferred from part-to-part of a piecemeal system.

SUMMARY

Briefly stated, torque devices according to implementations of the present disclosure obviate the shortfalls of piecemeal systems by reducing the number of part-to-part transitions of torque.

According to aspects of one or more exemplary implementations, disclosed is a torque-limiting driver comprising: a body having a handle; an upper cylindrical shank; a lower cylindrical shank having a drive socket; a nut; a spring between the upper cylindrical shank and the nut, wherein the spring is configured to apply a force across the upper cylindrical shank and the lower cylindrical shank; a shaft having a workpiece-engaging tip and a drive connection engaged within the drive socket of the lower cylindrical shank, the shaft extending axially through the lower cylindrical shank, the upper cylindrical shank, and the spring and connected to the nut, and the shaft having a lumen extending across an axial length of the shaft; wherein the upper cylindrical shank and the lower cylindrical shank engage for relative rotation, and wherein the upper cylindrical shank and the lower cylindrical shank disengage when a predetermined torque limit is exceeded.

The lumen may enclose a tube advanceable within the lumen. The tube may be configured to deliver a biologic material. The biologic material may be an adhesive such as a bone cement. The biologic material may be a growth stimulant. The lumen encloses a guidewire advanceable within the lumen. The drive socket may be a square drive socket and the drive connection may be a square drive connection. The shaft may include a threading that is threaded onto the nut. A force provided by the spring may securely maintain the drive connection of the shaft engaged within the drive socket of the lower cylindrical shank. The nut may include a lower portion having an outer diameter substantially equal to an inner diameter of the spring and extending axially through at least a portion of the spring.

The predetermined torque limit may be at least 1 inch-pound. The predetermined torque limit may be between about 70 inch-pounds and about 150 inch-pounds.

According to aspects of one or more exemplary implementations, disclosed is a method, comprising: providing to a workpiece a torque-limiting driver comprising: a body having a handle; an upper cylindrical shank; a lower cylindrical shank having a drive socket; a nut; a spring between the upper cylindrical shank and the nut, wherein the spring is configured to apply a force across the upper cylindrical shank and the lower cylindrical shank; a shaft having a workpiece-engaging tip and a drive connection engaged within the drive socket of the lower cylindrical shank, the shaft extending axially through the lower cylindrical shank, the upper cylindrical shank, and the spring and connected to the nut, and the shaft having a lumen extending across an axial length of the shaft; applying an applied torque to the torque-limiting driver, whereby the upper cylindrical shank and the lower cylindrical shank engage for relative rotation if the applied torque does not exceed the predetermined torque limit, and whereby the upper cylindrical shank and the lower cylindrical shank disengage if the applied torque exceeds the predetermined torque limit; and delivering a biologic material to the workpiece through the lumen.

According to aspects of one or more exemplary implementations, disclosed is a method, comprising: providing to a workpiece a torque-limiting driver comprising: a body having a handle; an upper cylindrical shank; a lower cylindrical shank having a drive socket; a nut; a spring between the upper cylindrical shank and the nut, wherein the spring is configured to apply a force across the upper cylindrical shank and the lower cylindrical shank; a shaft having a workpiece-engaging tip and a drive connection engaged within the drive socket of the lower cylindrical shank, the shaft extending axially through the lower cylindrical shank, the upper cylindrical shank, and the spring and connected to the nut, and the shaft having at least one lumen extending across an axial length of the shaft; wherein the upper cylindrical shank and the lower cylindrical shank engage for relative rotation, and wherein the upper cylindrical shank and the lower cylindrical shank disengage when a predetermined value of torque is exceeded; aligning the torque-limiting driver relative to the workpiece by use of a guidewire delivered through the lumen of the shaft; and applying an applied torque to the torque-limiting driver, whereby the upper cylindrical shank and the lower cylindrical shank engage for relative rotation if the applied torque does not exceed the predetermined torque limit, and whereby the upper cylindrical shank and the lower cylindrical shank disengage if the applied torque exceeds the predetermined torque limit.

According to one or more exemplary implementations said torque limiting driver may have at least one lumen forming a pathway from a proximal end of a driver to the distal end of the driver. Said at least one lumen extending axially through said nose cone and at least one of said upper shank, lower shank, locking screw, cap, and tip.

DRAWINGS

The above-mentioned features of the present disclosure will become more apparent with reference to the following description taken in conjunction with the accompanying drawings wherein like reference numerals denote like elements and in which:

FIG. 2A shows an exploded view of some aspects of a driver;

Figure 1:
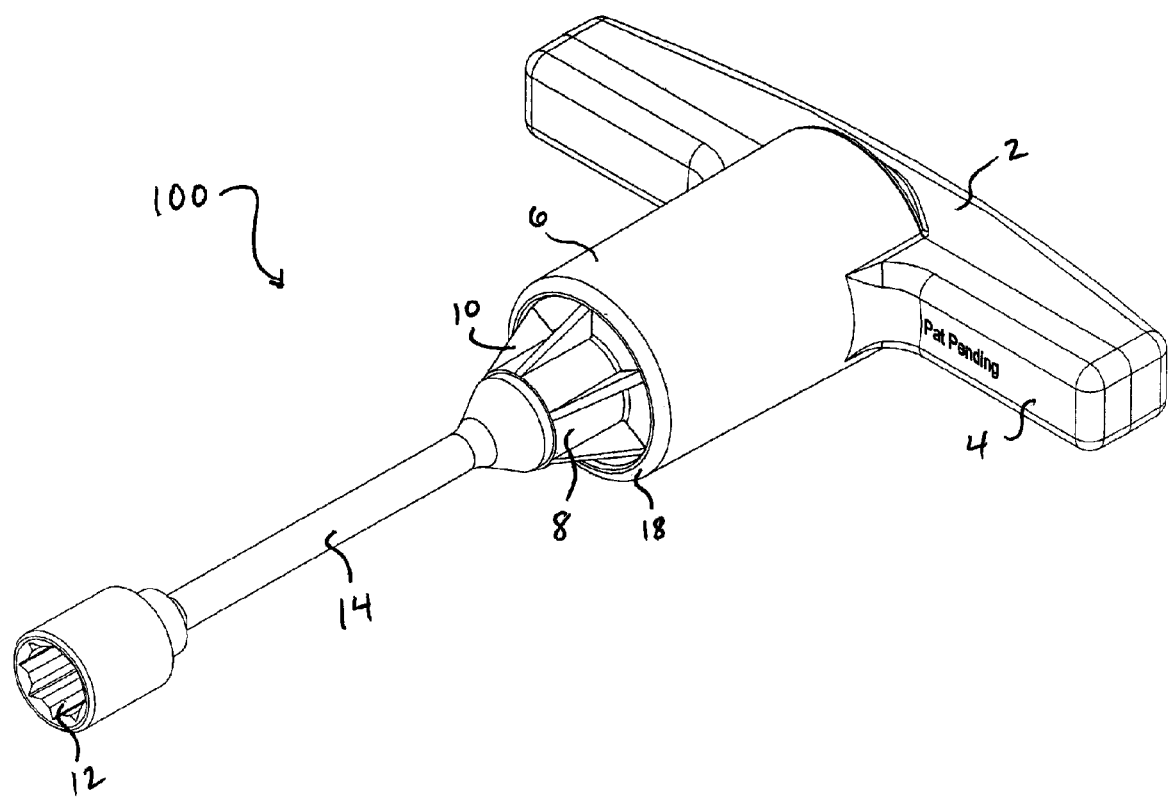
FIG. 1 shows a perspective view of some aspects of a driver.

As shall be appreciated by those having ordinary skill in the art, the figures are not to scale, and modifications to scale within a figure or across the figures are considered within the present disclosure.

FURTHER DESCRIPTION

According to one or more exemplary implementations, as shown in FIGS. 1-8, torque-limiting driver 100 may be provided. Torque-limiting driver 100 may have a generally T-shaped handle or other structure to facilitate use by a user. For example, the handle may by "T-shaped". The handle may include arms 4 at one end of an axially extending generally hollow cylindrical body 6. Cap 2 covers the same end of the handle. Cylindrical end 18 terminates cylindrical body 6 toward tip 12 of shaft 14. Cap 2 may be snap-fitted to cylindrical body 6, or may be welded, adhered, or attached by any equivalent thereof.

An exemplary implementation shows, at least in part, at cylindrical end 18, lower shank 700 provided, having an annularly tapering body and nose cone 8 along its length. Lower shank 700 may have a plurality of support flanges 10 that add strength while saving material. At one end, lower shank 700 tapers to drive socket 9 at the end of the nose cone 8 molded to engage drive connection 16 of shaft 14. An exemplary implementation shows, at least in part, shaft 14 provided, at one end, with workpiece-engaging tip 12, adapted for engagement with an associated workpiece, such as a fastener or the like. Workpiece-engaging tip 12 is shown to be a socket wrench, but could be a screwdriver, wrench, or any other surgical tool. At an opposite end, lower shank 700 has a plurality of teeth 82 arranged in a crown gear formation, with circumferential rim 31 extending radially outward and an internal axial bore to accommodate at least a portion of shaft 14 extending there through.

Figure 5:
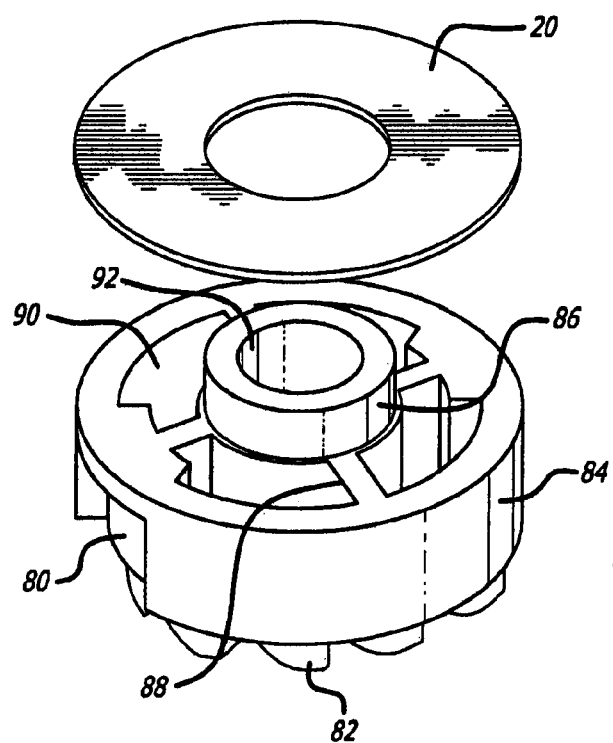
FIG. 5 shows a perspective view of some aspects of an upper shank.

According to aspects of one or more exemplary implementations, inside cylindrical body 6 a clutch assembly is disposed. The clutch assembly includes upper shank 800 for forcibly engaging lower shank 700. Upper shank 800 has a bottom face that has a plurality of teeth 82 arranged in a crown gear formation and circumferential rim 83 extending radially outward. As shown in FIG. 5, upper shank 800 includes outer cylindrical shank 84 and axial bore 92 through inner shank 86. Inner shank 86 and outer shank 84 are connected via inner supports 88, leaving upper shank 800 substantially hollow with internal spaces 90 on a top face. Alternatively, upper shank 800 may be of a single contiguous piece.

Figure 2B:
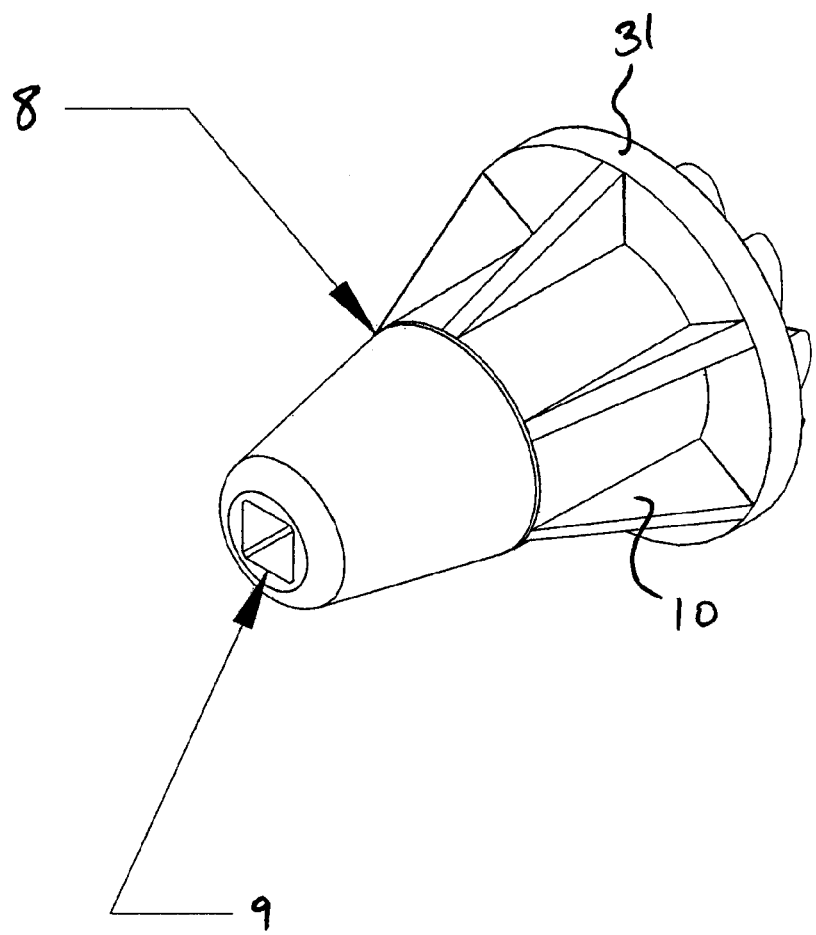
FIG. 2B shows a perspective view of some aspects of a nose cone.

According to one or more exemplary implementations, upper shank 800 includes at least one recess 80 on a side of outer shank 84. Recess 80 is provided as a cylindrical cut, relief or recess into the side of the outer shank and maybe provided as a square or rectangular cut or the cut may have a slanted side or sides relative to the axis of upper shank 800, as shown in FIG. 2.

In assembly, drive connection 16 of shaft 14 is received into drive socket 9 of lower shank 700. Washer 32 maybe provided between circumferential rim 31 of lower shank 700 and circumferential flange 30 extending radially inward within the hollow of cylindrical body 6. Washer 32 may be of a polymer or other material having low coefficient of friction. Alternatively, circumferential rim 31 of lower shank 700 may be provided flush against circumferential flange 30 of cylindrical body 6. The opposite side of circumferential flange 30 receives circumferential rim 83 of upper shank 800, allowing teeth 82 of lower shank 700 to engage teeth 82 of upper shank 800 when a torque is applied.

Figure 3:
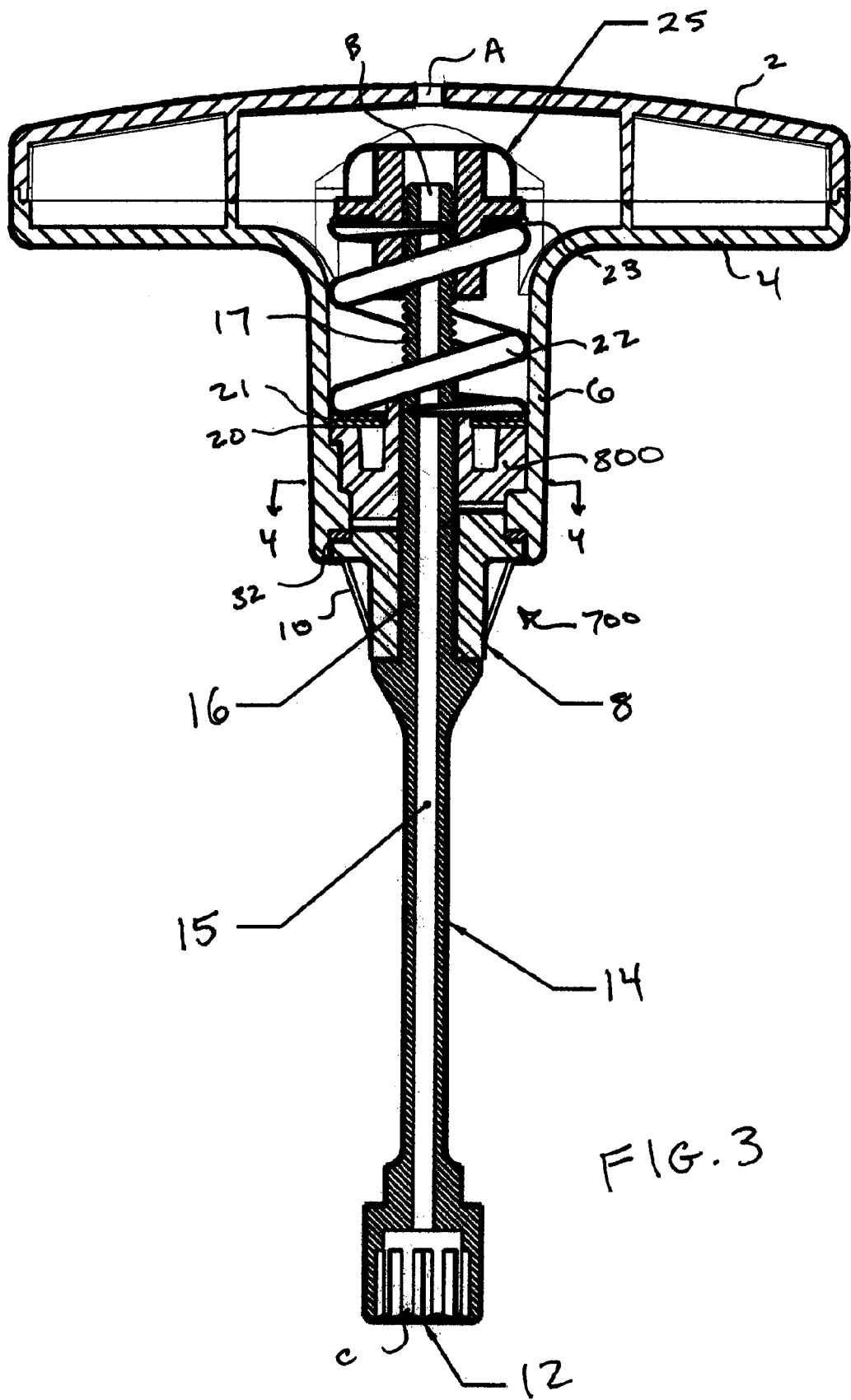
FIG. 3 shows a cross sectional view of some aspects of a driver.
Figure 4:
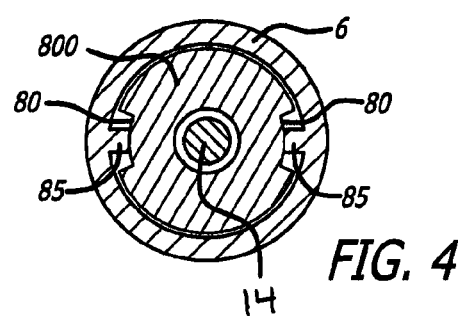
FIG. 4 shows a cross sectional view of some aspects of a driver.

According to aspects of one or more exemplary implementations, integrally formed within cylindrical body 6, protrusion 85 mates with recess 80 of upper shank 800. FIG. 3 and FIG. 4 illustrate protrusion 85 in relation with recess 80. Protrusion 85 extends inward in a radial fashion and has a length along the axis of cylindrical body 6 for relative moveable engagement within recess 80. This engagement provides a locking mechanism of shaft 14 relative to the handle via upper shank 800 when pressure is applied across lower shank 700 and upper shank 800. Recess 80 is provided circumferentially wider than protrusion 85 for allowing cylindrical body 6 and the handle to rotate in reverse a predetermined distance from a locked position without subsequent reverse rotation of workpiece-engaging tip 12. Thus, at least one recess 80 and at least one protrusion 85 lock the handle in one direction providing the necessary torque to drive a fastener and allow for a predetermined amount of reverse rotation before unscrewing the fastener.

According to aspects of one or more exemplary implementations, force is applied across lower shank 700 and upper shank 800 via spring 22 within cylindrical body 6. Inside cylindrical body 6, shown in FIG. 2 and FIG. 5, washer 20 and washer 21 are provided between upper shank 800 and spring 22. Washer 20 and washer 21 transfer pressure from spring 22 over the top face of upper shank 800. At an end of spring 22 opposite upper shank 800, washer 23 and nut 25 hold spring 22 in a relatively compressed state. Washer 23 may be provided between nut 25 and spring 22 to facilitate relative rotation of nut 25 and spring 22.

According to one or more exemplary implementations, shaft 14 having threading 17 at an end opposite workpiece-engaging tip 12 engages a complementary threading within nut 25, thereby imparting pressure between the respective teeth 82 of lower shank 700 and upper shank 800. Spring 22 and nut 25 provide the proper tensioning and biasing for the clutch assembly and, generally, the nut 25 is adjustable relative to shaft 14 to provide proper tension and calibration.

According to aspects of one or more exemplary implementations, various materials may be used for the components of driver 100. According to some exemplary implementations, at least one of body 6, nut 25, lower shank 700, and upper shank 800 is of a plastic material or a composite including plastic. Plastic and other economical equivalents improve cost efficiency of production while providing high tensile strength, resistance to deformation, etc. Effective materials include plastics, resins, polymers, imides, fluoropolymers, thermoplastic polymers, thermosetting plastics, and the like as well as blends or mixtures thereof. According to aspects of one or more exemplary implementations, at least one of lower shank 700 and upper shank 800 is of or includes at least one material that lubricous or otherwise reduces friction. The presence of a friction-reducing material allows geometric aspects of the engagement between lower shank 700 and upper shank 800 to govern whether teeth engage or disengage, thereby improving precision of the device.

According to aspects of one or more exemplary implementations, materials and components of drive 100 are resistant to sterilization, cleaning, and preparation operations at a surgical site. . For example, drive 100 and parts thereof are configured to withstand sterilization by methods including radiation (e.g., gamma rays, electron beam processing), steam (e.g., autoclave), detergents, chemical (e.g., Ethylene Oxide), heat, pressure, inter alfa. For example, materials for drive 100 may be selected according to resistance to one or more selected sterilization techniques.

According to aspects of one or more exemplary implementations, shaft 14 is of a rigid material. For example, shaft 14 may be of a metal, such as stainless steel. According to some exemplary implementations, high torque capabilities of drive 100 are, at least in part, provided by features that maintain an effective engagement between drive connection 16 of shaft 14 and drive socket 9 of lower shank 800. For example, some exemplary implementations are provided to improve the ability of drive 100 to maintain its grip on shaft 14 up to a greater range of torque.

According to aspects of one or more exemplary implementations, a single integrated shaft 14 spans the distance between workpiece-engaging tip 12 and an engagement point with nut 25. This configuration enables greater torque capabilities than a piecemeal or fragmented set of interconnected components. This reduces the number of interconnections between a source of a torque and a location to which the torque is transferred.

According to one or more exemplary implementations, shaft 14 having drive connection 16 between opposing extensions stabilizes drive connection 16 within drive socket 9. Placement of drive connection 16 at a medial segment of shaft 14, rather than at an end thereof, facilitates a more stable engagement between drive connection 16 and drive socket 9, thereby increasing the ability of engagement to transfer high amounts of torque.

According to one or more exemplary implementations, an engagement of drive connection 16 within drive socket 9 is maintained by the connection of the integrated portion of shaft 14 that extends to nut 25. According to some exemplary implementations, both threading 17 and drive connection 16 are of a single integrated structure (i.e., shaft 14). A force applied by spring 22 to nut 25 is directly transferred along shaft 14 from threading 17 to drive connection 16. This force securely maintains drive connection 16 within drive socket 9. This engagement enables transfers of greater amounts of torque from lower shank 700 (i.e., via drive socket 9) to shaft 14 (i.e., via drive connection 16).

According to aspects of some exemplary implementations, drive connection 16 and drive socket 9 have complementary geometries. One or more of a variety of configurations may be provided for engaging drive connection 16 within drive socket 9. For example drives and associated connections may include triangular, square, hexagonal, rectangular, etc. According to aspects of one or more exemplary implementations, a substantially square drive connection 16 and drive socket 9 provide high torque transfer capabilities. Out of a variety of drive types, experimental results demonstrated that square drives and connections were among the most successful at transferring high torque without failure. Drive connection 16 and drive socket 9 may have rounded corners and edges to reduce or distribute stress risers.

According to aspects of one or more exemplary implementations, driver 100 capable of transferring higher torque may be provided with spring 22 having a greater spring constant (i.e., force constant) or otherwise be calibrated with spring 22 exerting greater forces in an initial (rest) state. A more robust spring 22, washer 20 and washer 21 may both be provided where spring 22 may have a tendency to grip relative to washer 21. A more robust spring 22 increases the probability of a friction grip relative to washer 21. Provision of additional washer 20 preserves at least one free-spinning structure between spring 22 and upper shank 800.

According to aspects of one or more exemplary implementations, nut 25 may provide a lower portion having outer diameter substantially equal to an inner diameter of spring 22. The lower portion of nut 25 may extend axially through at least a portion of spring 22. The lower portion of nut 25 may maintain relative axial alignment between nut 25 and spring 22 by limiting travel of spring 22 other than by compression thereof.

Figure 6:
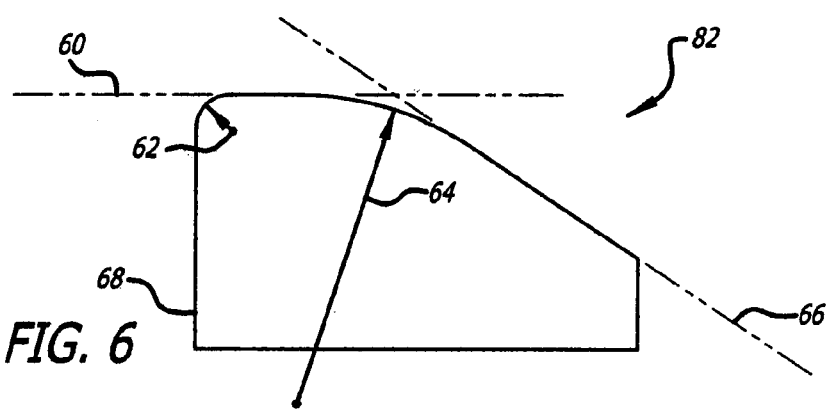
FIG. 6 shows a profile view of some aspects of a tooth from a clutch assembly.
Figure 7:
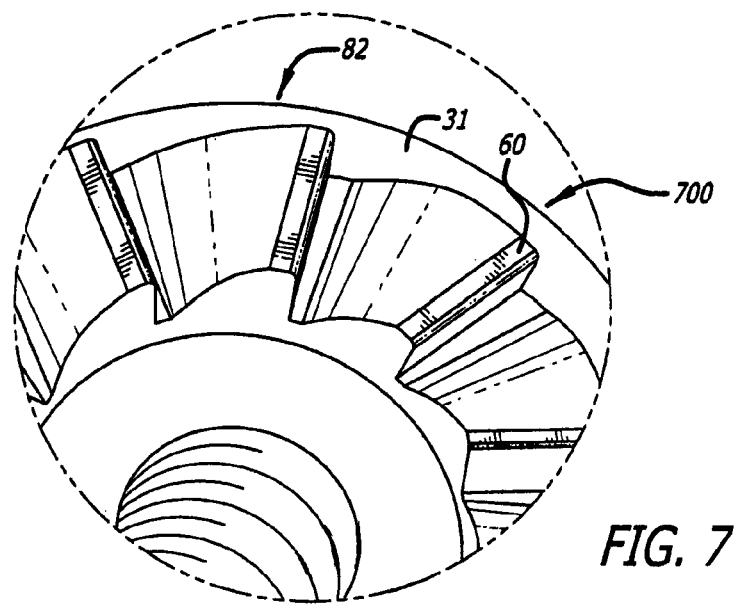
FIG. 7 shows a perspective view of some aspects of the teeth from a clutch assembly.
Figure 8:
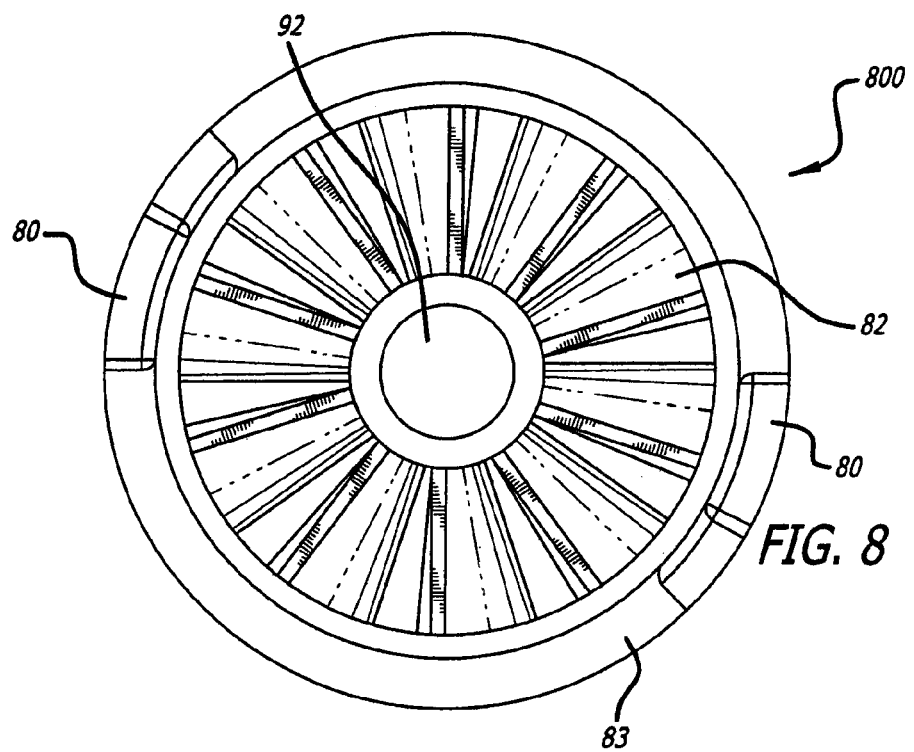
FIG. 8 shows a top view of some aspects of the teeth from a clutch assembly.

According to aspects of one or more exemplary implementations, the plurality of teeth 82 are formed on the top face of lower shank 700 and the bottom face of upper shank 800 to forcibly engage to impart torque from the handle to the workpiece when a torque is applied. Referring to FIGS. 6 and 7, tooth 82 has inclined face 66 that smoothly transitions to substantially flat peak 60, via first radius of curvature 64. Substantially flat peak 60 subsequently transitions smoothly, via second radius of curvature 62, to vertical face 68 that is substantially parallel to the axis of lower shank 700 and upper shank 800. First radius of curvature 64 is typically much larger than second radius of curvature 62.

Experimental results have shown that a tooth having an inclined face that smoothly transitions to a substantially flat face is capable of imparting a substantial increase in torque to a fastener. In one experiment, a ten-fold increase in torque was observed. This increase in torque is due to the frictional forces associated with the smoothly transitioning curve of inclined face 66 of teeth 82.

In a simplified example, when two uniform inclines are frictionally engaged, only one static force, having a single coefficient of static force, is acting against the relative movement of the two inclines. However, when the two inclines are not uniform, more than one coefficient of static force can be observed, thus resulting in a higher disinclination to movement.

According to aspects of one or more exemplary implementations, teeth 82 are circumferentially spaced in a crown gear formation of the top face and bottom face of lower shank 700 and upper shank 800, respectively. Teeth 82 are preferably configured in a spiral formation, as shown in FIG. 7. Each face of lower shank 700 and upper shank 800 has an inner radius and an outer radius and teeth 82 spiral around the inner radius resulting in a larger tooth detail when viewing the tooth from the outer radius relative to the tooth detail when viewing the tooth from the inner radius. The spiral configuration of teeth 82 can also be defined as having a longer inclined face 66 at the edge of the tooth on or near the outer radius relative to inclined face 66 at the edge of the tooth on or near the inner radius of lower shank 700 and upper shank 800. Results have shown that teeth arranged in said spiral configuration provide an increased reliability and/or precision in torque consistency when compared to non-spiral counterparts.

Substantially flat peaks 60 of teeth 82 may be as wide at the inner radius as they are at the outer radius. Alternatively, substantially flat peaks 60 may be wider at the outer radius and taper toward the inner radius.

Vertical faces 68 of teeth 82 of lower shank 700 and upper shank 800 respectively engage when a torque is applied to prevent relative rotation of lower shank 700 and upper shank 800 in one direction. Inclined faces 66 engage to accommodate relative rotation of lower shank 700 and upper shank 800 in an opposite direction.

According to aspects of one or more exemplary implementations, the extent to which threading 17 of shaft 14 is threaded into nut 25 controls the amount of compression or preload on spring 22 which, subsequently, controls the limiting torque required to effect relative rotation of lower shank 700 and upper shank 800. If shaft 14 is more deeply threaded into nut 25, then a higher torque will be required to disengage teeth 82 of lower shank 700 and upper shank 800. If shaft 14 is less deeply threaded into nut 25, then a lower torque will be required to disengage teeth 82 of lower shank 700 and upper shank 800. Accordingly, a predetermined torque limit is selectively programmable. The predetermined torque limit may correspond to a predefined threshold of a workpiece (e.g., a fastener) having a desired level of torque-based installation not to be exceeded.

According to one or more exemplary implementations, when driver 100 is rotated in one direction under an applied torque, shaft 14 will rotate with cylindrical body 6 and handle until a predetermined torque limit is reached. When the predetermined torque limit is reached or exceeded by the applied torque, a biasing force exerted by spring 22 will be overcome, allowing inclined face 66 of upper shank 800 to slide up a respective inclined face 66 of lower shank 700, subsequently snapping each tooth 82 of lower shank 700 into engagement behind a next tooth 82 of upper shank 800. This snapping sound is typically an audible indication to a user that a predetermined torque limit has been reached or exceeded.

When a force beyond the predetermined torque limit is achieved, teeth 82 of lower shank 700 and upper shank 800 will continue to disengage, resulting in rotation of the handle with no further rotation of workpiece-engaging tip 12. Thus, the handle will continue to rotate, disengaging teeth 82 with every rotational movement that will not impart continued force beyond a predefined threshold to the fastener.

According to one or more exemplary implementations, when driver 100 is rotated in the opposite direction, the handle rotates in reverse a predetermined distance from a locked position without subsequent reverse rotation of workpiece-engaging tip 12. However, when protrusion 85 travels the provided distance within recess 80 and locks against the opposite end of recess 80, driver 100 will operate as a standard driver with no torque-limiting feature since engaging vertical face 68 will force relative rotation of lower shank 700 and upper shank 800 in the opposite direction without any torque-limiting feature.

According to aspects of one or more exemplary implementations, the disposable torque-limiting driver of the present disclosure is capable of imparting torques of up to about 120 inch-pounds. For example, the torque output range may be selected between about 70 inch-pounds and about 120 inch-pounds. Typically, the torque requirement is different for different operations and for different implants. For example, applications may include those in the field of orthopedic surgery, construction and emplacement of implants, etc. Therefore, in some instances, the predetermined torque limit maybe at least about 1 inch-pound. In other instances, the predetermined torque limit may be between about 5 inch-pounds and about 150 inch-pounds, depending on an implant's specifications. In other instances, the predetermined torque limit may be between about 70 inch-pounds and about 120 inch-pounds, depending on an implant's specifications.

According to one or more exemplary implementations, as shown in FIG. 3, shaft 14 may be cannulated to include lumen 15. Lumen 15 may extend along the entire length of shaft 14, with a top opening "B" and a bottom opening "C" (at workpiece-engaging tip 12), said openings in some instances being in fluid communicating with each other. Body 6 may provide access to lumen 15, such as via aperture "A" of cap 2. According to some exemplary implementations, lumen 15 may accommodate one or more devices or materials for use in tandem with the torque capabilities of driver 100. According to some exemplary implementations, a guidewire to aide in driver alignment may be provided through lumen 15. According to some exemplary implementations, lumen 15 may accommodate a removable tube delivering a biologic material to be dispensed before, during, or after torque is applied during surgery. For example, the biologic material could be an adhesive to assist in locking or staking a fastener to which torque was applied. By further example, the biologic material may assist in stimulation of bone growth (i.e., growth stimulant) in a subject. Lumen 15 may accommodate one or more devices 400. Such devices 400 may include a sound-emitting device (e.g., ultrasound, etc.), a radiation-emitting device (e.g., light, laser, LED, etc.), a drilling device, a cutting device, an ablation device, a curing device, a retrieval device, an aspiration device, a suction device, an irrigation device, a gasification device, a cooling device, a heating device, an optical device (e.g., scope for viewing, etc.) at a surgical site, inter alia. Those of ordinary skill in the art will recognize that such devices 400 are to be removably inserted and retrieved from said lumen.

Figure 9:
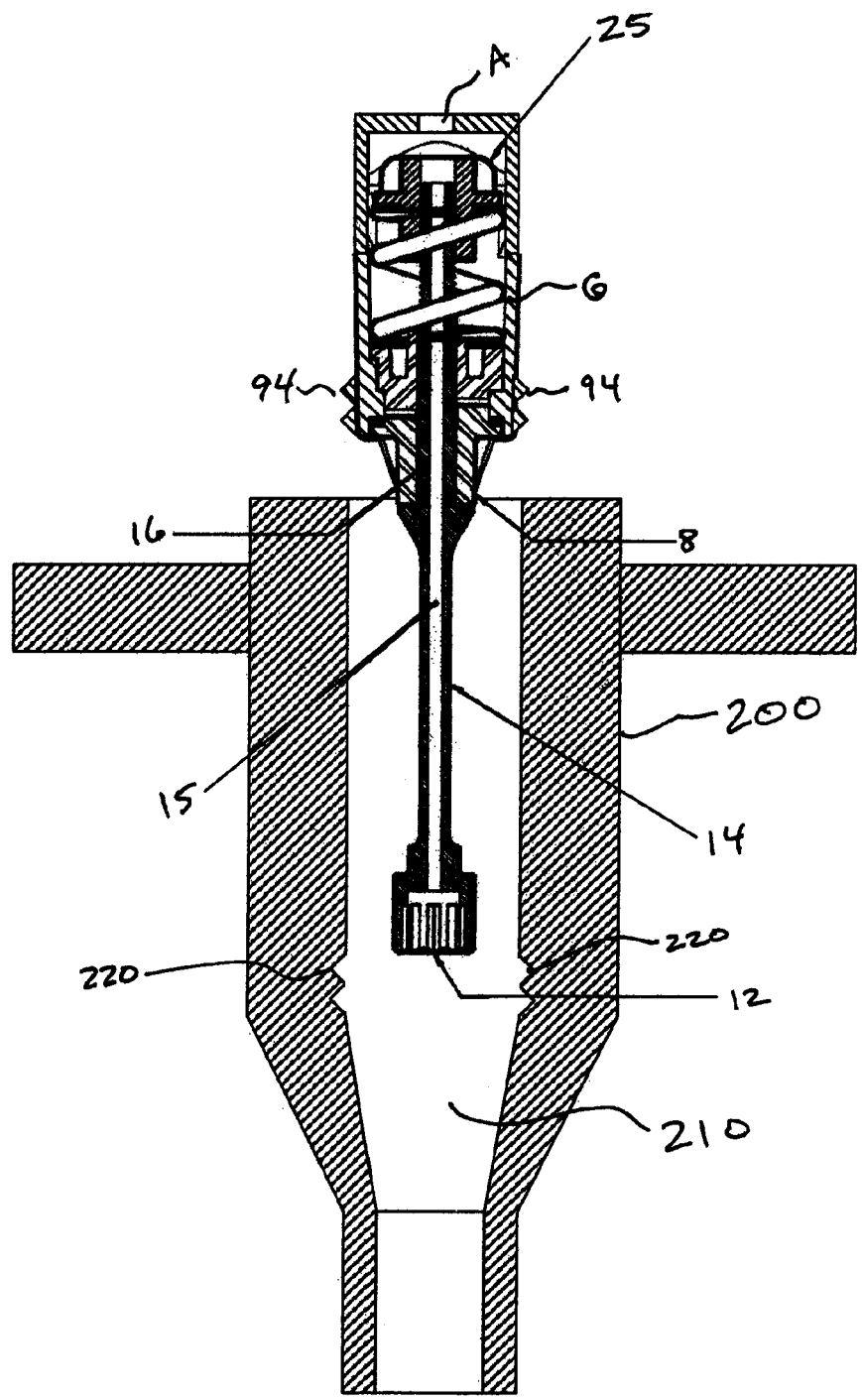
FIG. 9 shows a cross sectional view of some aspects of a driver and an operation tool.
Figure 10:
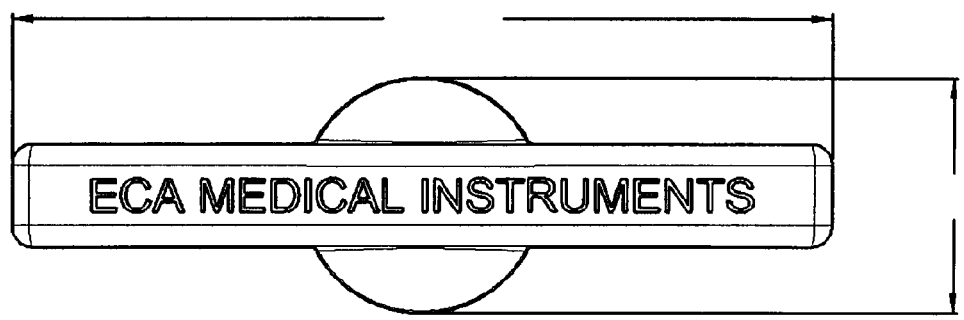
FIG. 10 shows a top view of some aspects of a driver.
Figure 11:
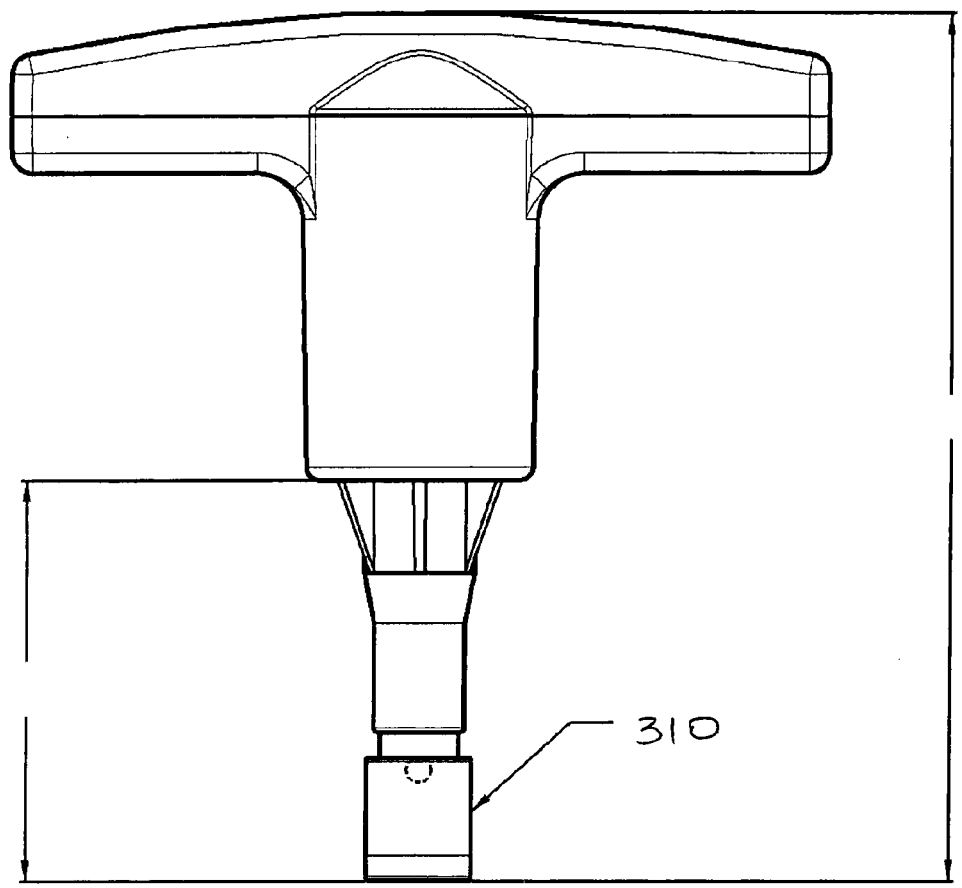
FIG. 11 shows a side view of some aspects of a driver.

According to one or more exemplary implementations, as shown in FIG. 9, driver 100 may be configured to interface with at least one other device. For example, as shown in FIG. 9, driver 100 may be a device that selectably fits, at least partially, within channel 210 of operation tool 200. Operation tool 200 is a body with a channel such as a lumen in a cannula. Operational tool 200 may be configured to accept one or more devices, including driver 100, wherein such devices are selectably interchangeable during a procedure. According to aspects of one or more exemplary implementations, operation tool 200 may include female interface 220 configured to mate with male interface 94 of driver 100. Male interface 94 and female interface 220 may provide selectably secure engagement between driver 100 and operation tool 200 via threading, friction, interference fitting, locks, gears, snaps, pins, and the like. Male interface 94 and female interface 220 may limit one or more of relative axial motion, relative radial motion, and relative rotational motion between driver 100 and operation tool 200.

According to aspects of one or more exemplary implementations, driver 100 may deliver torque while within operation tool 200. According to aspects of one or more exemplary implementations, driver 100 is rotatable according to the rotation of operation tool 200. For example, body 6 of driver 100 may be rotationally fixed relative to operation tool 200, such that rotation of operation tool 200 results in rotation of body 6, imparting programmable torque at tip 12. According to aspects of one or more exemplary implementations, driver 100 is rotatable independent of the rotation of operation tool 200. For example, body 6 of driver 100 may be rotated within operation tool 200 while operation tool 200 is held in place, wherein driver 100 imparts programmable torque at tip 12.

According to one or more exemplary implementations, driver 100 may be interchanged within operation tool 200 with other devices. Operation tool 200 may provide a stable platform for a variety of devices to perform designated functions. Across the variety of devices, operation tool 200 may maintain constant or selectable location and orientation for controllably aligning and delivering the devices to a desired location.

In some instances, a torque-limiting driver, such as driver 100, may be prepackaged with an implant provided for one-time use. Such a methodology matches the driver that will impart a required amount of torque with the implant.

In other instances, driver 100 may be reusable. Shaft 14 may be interchangeably fixed relative to nose cone 8 for the accommodation of multiple workpiece-engaging tips 12. It is also to be appreciated that the handle of the driver is not limited to a T-shape and may be provided in any other suitable configuration.

Figure 12:
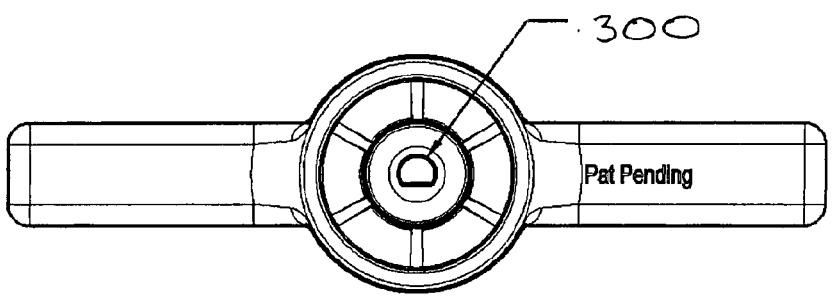
FIG. 12 shows a bottom view of some aspects of a driver.
Figure 13:
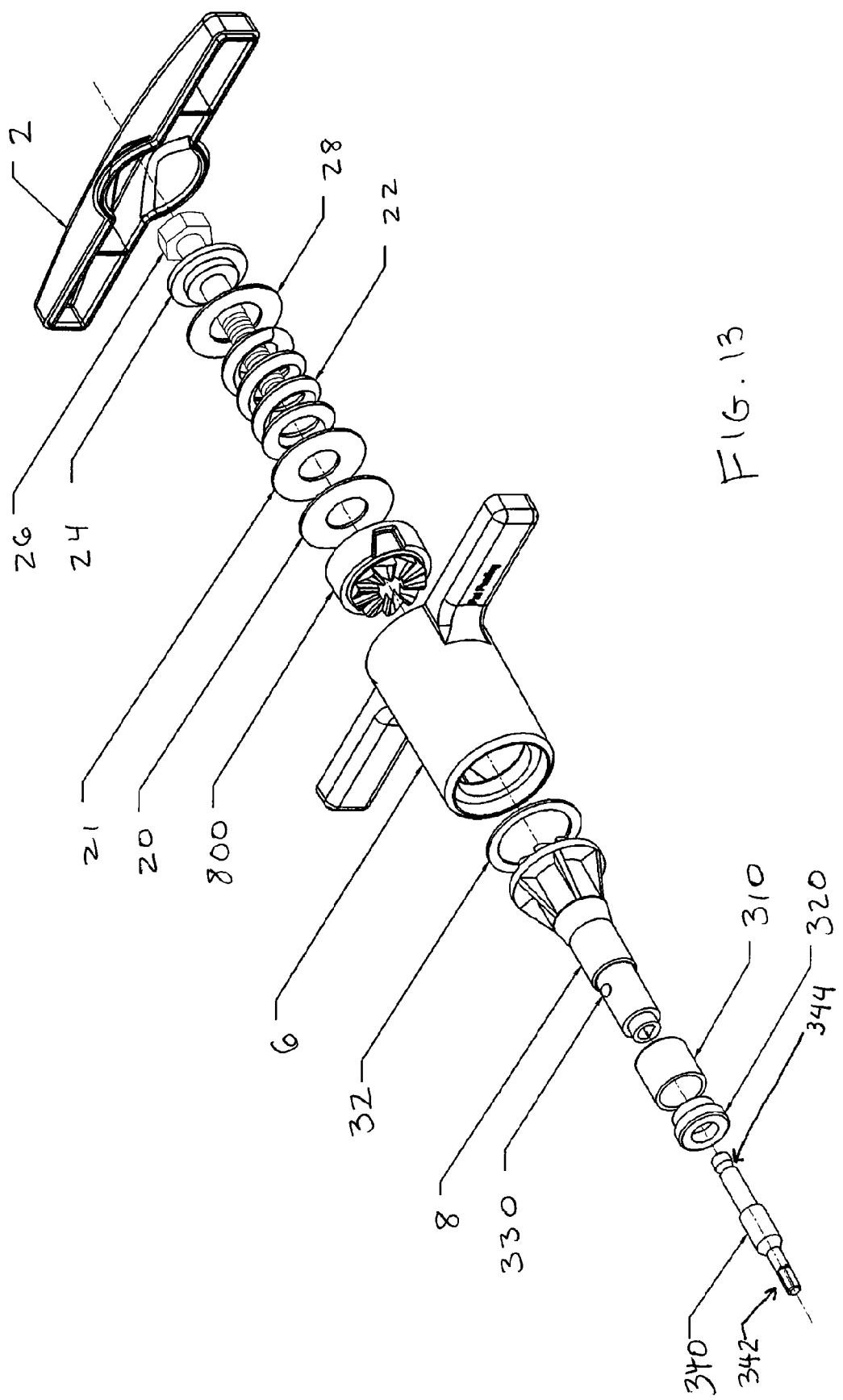
FIG. 13 shows an exploded view of some aspects of a driver.
Figure 14:
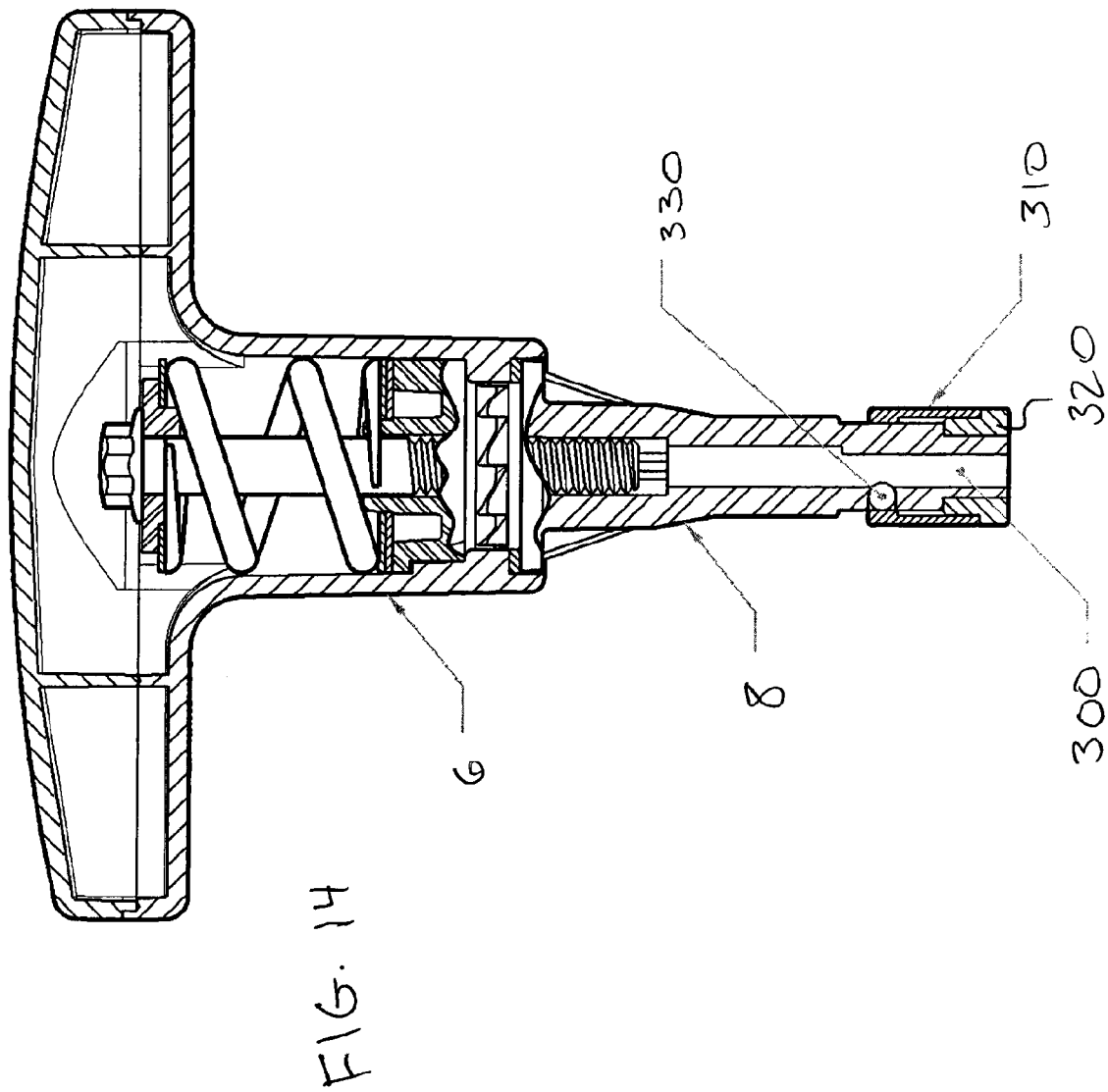
FIG. 14 shows a cross sectional view of some aspects of a driver.
Figure 15:
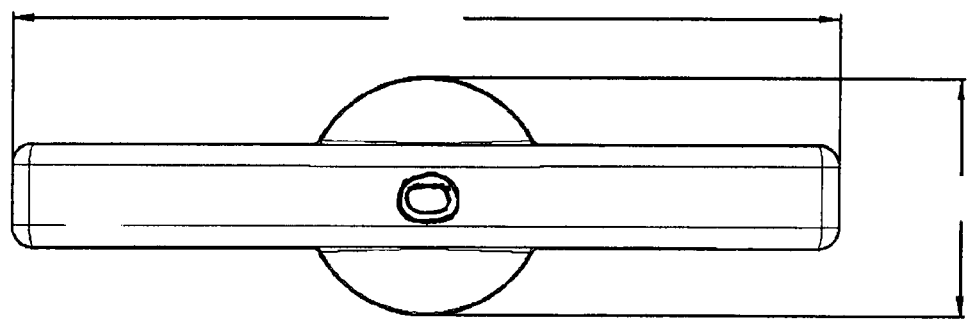
FIG. 15 shows a top view of some aspects of a driver.
Figure 16:
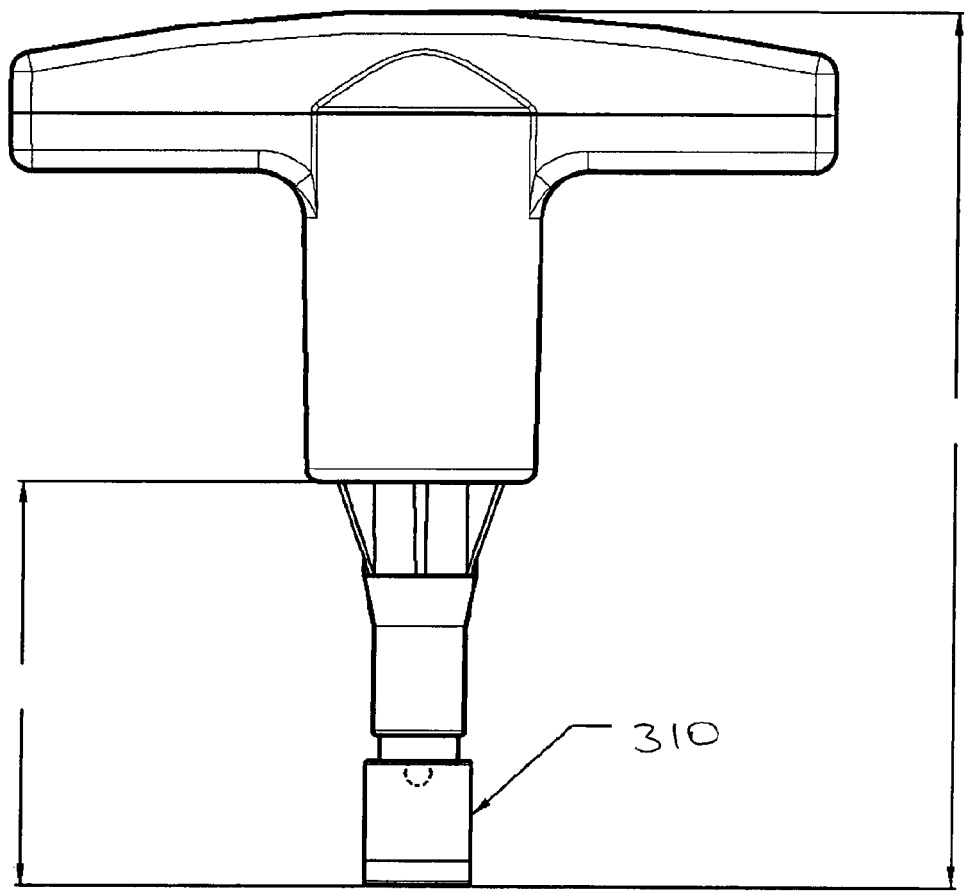
FIG. 16 shows a side view of some aspects of a driver.
Figure 17:
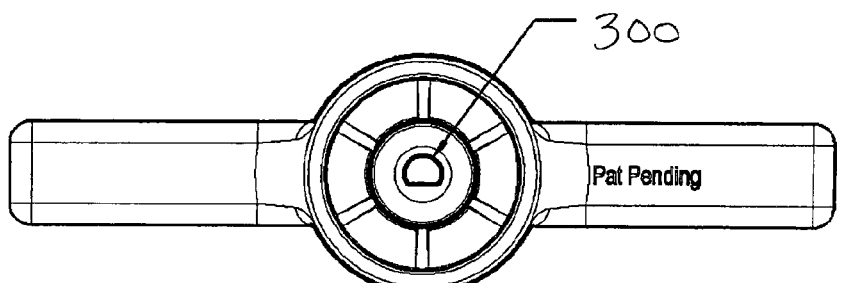
FIG. 17 shows a bottom view of some aspects of a driver.
Figure 18:
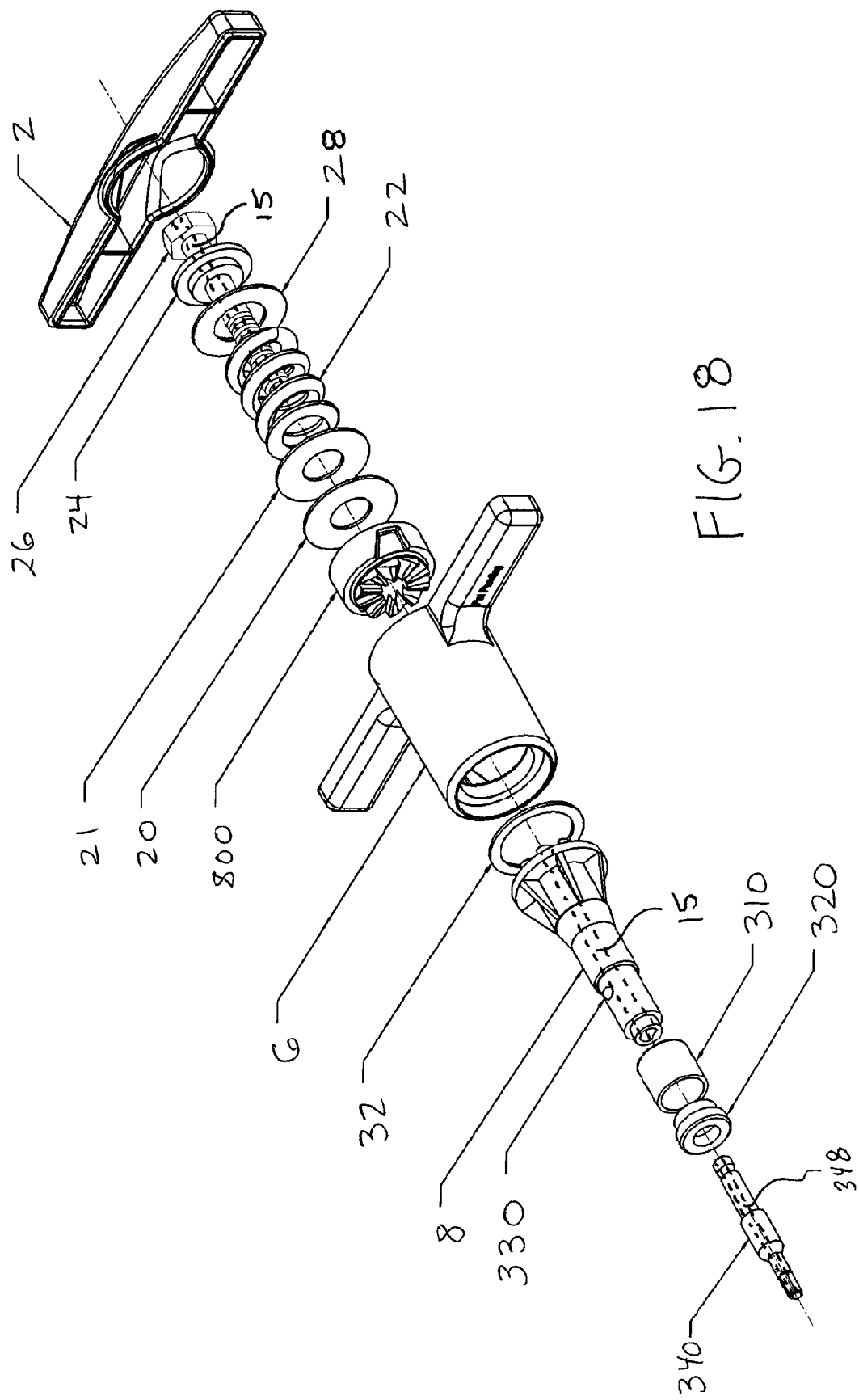
FIG. 18 shows an exploded view of some aspects of a driver.

According to one or more exemplary implementations, as shown in FIGS. 10, 11, 12, 13, and 14, customizable connections for removable tips may be provided. For example, as shown in FIGS. 12, 13, and 14, A-O hole 300 may be provided at a distal end of driver 100. A-O hole 300 may be part of or defined by a recess within nose cone 8. A-O hole 300 is configured to receive A-O tip 340, as shown in FIG. 13. "A-O" is a known designator of a connection mount consisting of a partial circular wall and a substantially flat section of wall, sometimes referred to as "D" shaped, to form a guide (catch) or mount for a corresponding tip or elongated member (latch). The A-O tip may have a additional mount for other tools at its remote end 342.

According to one or more exemplary implementations, lower shank 700 is integrally connected to or otherwise coupled with nose cone 8. Accordingly, torque transferred to lower shank 700 may be further transferred along nose cone 8 to A-O tip 340.

A-O hole 300 may be radially symmetric, radially asymmetric, or geometric. For example, as shown in FIG. 12, A-O hole 300 may allow entry of A-O tip 340 in only one orientation by providing a radially asymmetric shape as viewed in cross section. As shown, A-O hole 300 may be D-shaped, with at least a portion of A-O tip 340 having complementary shape, thereby providing mating capabilities.

According to one or more exemplary implementations, nose cone 8 includes ball bearing 330. Ball bearing 330 is selectively and at least partially protruding into A-O mounting hole 300. For example, ball bearing 330 may protrude in a manner that controllably locks or secures tip 340 axially within A-O hole 300. A-O tip 340 may have a corresponding recess or other geometry to receive at least a portion of ball bearing 330 when inserted a sufficient axial distance within A-O hole 300. Likewise, the portion of ball bearing 330 protruding into A-O hole 300 may be pushed at least somewhat out of A-O hole 300 by portions of A-O tip 340 as it is being inserted into A-O hole 300 until a catch 344 such as a grove formed on said A-O tip is aligned with said ball bearing 330 A-O tip. For example, ball bearing 330 may return to a protruding state when A-O tip 340 is properly inserted within A-O hole 300.

According to one or more exemplary implementations, as shown in FIG. 14, release shroud 310 covers at least a portion of nose cone 8 and at least a portion of ball bearing 330. Release shroud 310 may be opposite the portion of ball bearing 330 that protrudes into A-O hole 300. Release shroud 310 may tend to cause at least a portion of ball bearing 330 to protrude into A-O hole 300. Release shroud 310 may be a covering, a spring, a pin, or any other device that applies some force to ball bearing 330. Release shroud 310 shown in FIGS. 13 and 14 may be of a flexible or semi-flexible material, such as plastics, such that is provides some play or motion of ball bearing 330 while providing a force that tends to maintain a portion thereof protruding within A-O hole 300.

Components may be provided to maintain a position or orientation of release shroud 310. For example, end cap 320 is configured to maintain release shroud 310 in an axial position relative to nose cone 8. As shown in FIG. 14, end cap 320 may be fixed to a distal end of nose cone 8.

According to one or more exemplary implementations, as shown in FIGS. 15, 16, 17, 18, and 19, driver 100 and components thereof may have one or more lumens or form cannula and include one or more lumens providing access to a distally-located worksite from a proximal end of driver 100. Access may be provided through the one or more lumens disposed along a central axis of driver 100. Lumens may extend axially through at least one of nose cone 8, upper shank 800, lower shank 700, locking screw 26, cap 2, and tip 340. A plurality of lumens may form a pathway from a distal end of driver 100 to a proximal end of driver 100. A plurality of lumens may form a pathway from a distal end of driver 100 to a proximal end of driver 100 and extend axially through at least one of nose cone 8, upper shank 800, lower shank 700, locking screw 26, cap 2, and tip 340. A plurality of lumens may form a pathway from a distal end of driver 100 to a proximal end of driver 100 and at least one lumen extend axially through at least one of nose cone 8, upper shank 800, lower shank 700, locking screw 26, cap 2, and tip 340 to a surgical site.

Figure 19:
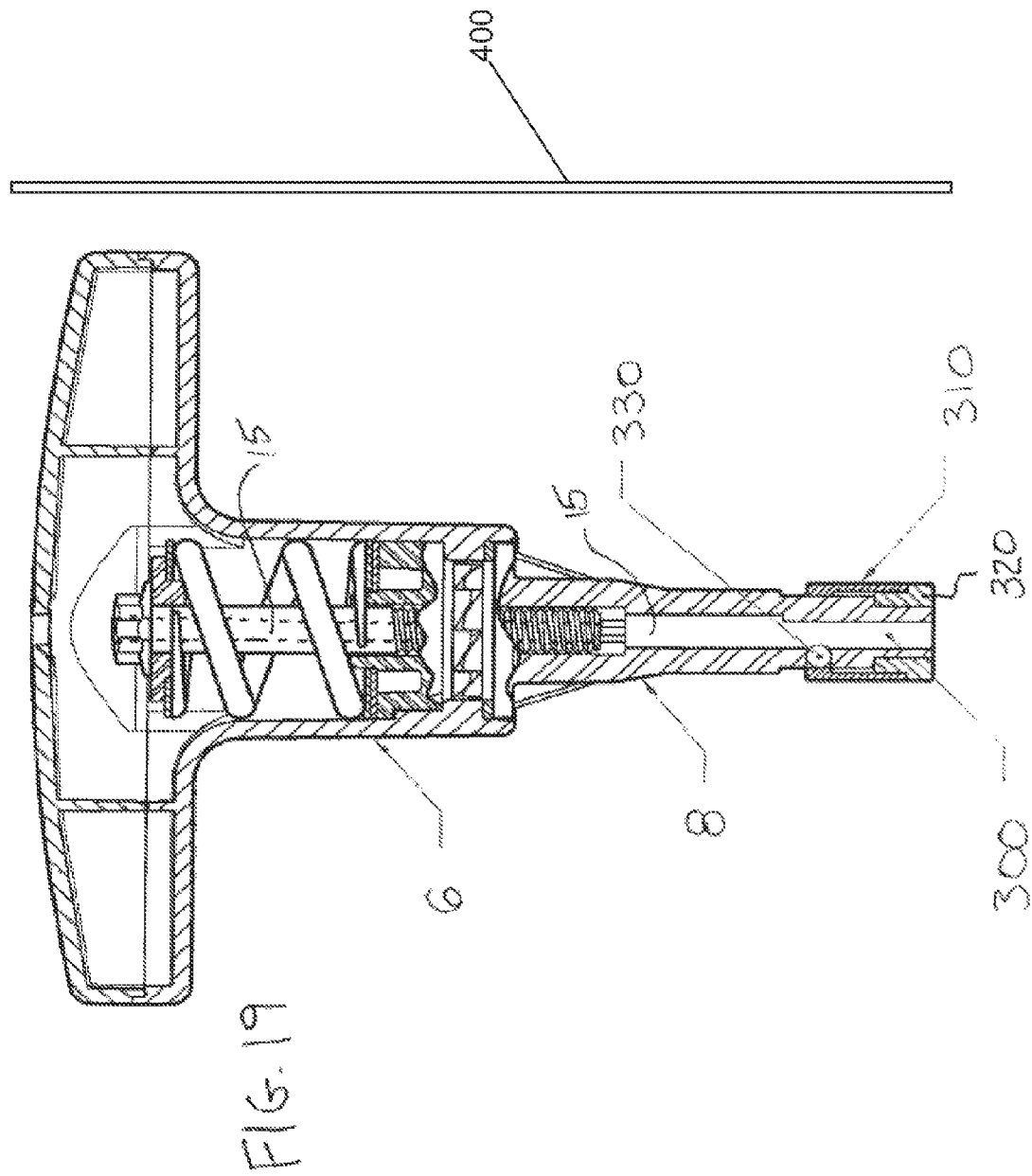
FIG. 19 shows a cross sectional view of some aspects of a driver.

For example, as shown in FIG. 19, lumen 15 extends through locking screw 26 and nose cone 8, wherein it may connect to a lumen within A-O tip 340. Locking screw may extend through or around spring 22 to secure to or thread within lower shank 700, and spring 22 may apply a force across upper shank 800 and lower shank 700. Accordingly, lumen 15 extending through locking screw 26 and nose cone 8 may connect to A-O tip 340. A-O tip 340 having a tip lumen 348 aligned with said lumen 15. Usage of lumen 15 may be according to usages as disclosed further herein. For example, lumen 15 may be used for delivering, to a surgical site, biologic materials, adhesives, cements, devices 400, tools, medicines, therapies, etc.

While the method and agent have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A torque-limiting driver for driving a workpiece, comprising:
    a generally hollow cylindrical body;
    a nose cone at one end of said body;
    within said body an upper shank;
    within said body a lower shank, the lower shank being integrally connected to said nose cone;
    said nose cone having a recessed hole configured to receive a workpiece-engaging tip;
    within said body, a locking screw extending through the upper shank and coupled to the lower shank;
    within said body, a spring between a portion of the locking screw and the upper shank, the spring applying a force across the upper shank and the lower shank;
    wherein the upper shank and the lower shank have a plurality of teeth forming a pair a crown gears and an axial bore that defines an inner radius of the upper and lower shank, the axial bore being coaxially aligned with the recessed hole;

wherein the teeth of the upper and lower shank forcibly engage for relative upper and lower shank rotation and wherein the teeth disengage when a predetermined value of torque applied to said body is exceeded; and, at least one lumen extending axially through the nose cone coaxially within said recessed hole, and said at least one lumen extending axially through at least one of the upper shank, the lower shank, and the locking screw.

2. The torque limiting driver of claim 1, further comprising one or more devices insertable through said at least one lumen and a second lumen disposed within the workpiece-engaging tip.

3. The torque limiting driver of claim 2, wherein each of said devices is one of a sound-emitting device, a radiation-emitting device, a drilling device, a cutting device, an ablation device, a curing device, a retrieval device, an aspiration device, a suction device, an irrigation device, a gasification device, a cooling device, a heating device, and an optical device.

* * * * *